(12) United States Patent
Scott

(10) Patent No.: US 10,646,526 B2
(45) Date of Patent: *May 12, 2020

(54) CANNABIS EXTRACTION METHOD AND COMPOSITIONS

(71) Applicant: ST&T International, Inc., Zephyr Cove, NV (US)

(72) Inventor: Michael Scott, Zephyr Cove, NV (US)

(73) Assignee: ST&T INTERNATIONAL, INC., Zephyr Cove, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/382,629

(22) Filed: Apr. 12, 2019

(65) Prior Publication Data

US 2019/0240272 A1    Aug. 8, 2019

Related U.S. Application Data

(63) Continuation of application No. 15/037,817, filed as application No. PCT/US2015/019699 on Mar. 10, 2015, now Pat. No. 10,307,446.

(60) Provisional application No. 61/968,893, filed on Mar. 21, 2014.

(51) Int. Cl.
| | |
|---|---|
| *A61K 36/00* | (2006.01) |
| *A61K 36/185* | (2006.01) |
| *A61K 36/886* | (2006.01) |
| *A61K 9/00* | (2006.01) |

(52) U.S. Cl.
CPC .......... *A61K 36/185* (2013.01); *A61K 9/0014* (2013.01); *A61K 36/886* (2013.01); *A61K 2236/00* (2013.01)

(58) Field of Classification Search
CPC .................................................... A61K 36/00
USPC ......................................................... 424/725
See application file for complete search history.

(56) References Cited

U.S. PATENT DOCUMENTS

| | | |
|---|---|---|
| 4,957,907 A | 9/1990 | McAnalley |
| 5,747,352 A | 5/1998 | Yan et al. |
| 5,910,419 A | 6/1999 | Johnson et al. |
| 6,720,192 B1 | 4/2004 | Viel et al. |
| 6,730,519 B2 | 5/2004 | Elsohly et al. |
| 7,344,736 B2 | 3/2008 | Whittle et al. |
| 7,622,140 B2 | 11/2009 | Whittle et al. |
| 7,749,712 B2 | 7/2010 | Pulli et al. |
| 8,337,908 B2 | 12/2012 | Letzel et al. |
| 8,343,553 B2 | 1/2013 | Hospodor |
| 8,512,767 B2 | 8/2013 | Ross |
| 8,518,653 B2 | 8/2013 | Takkinen et al. |
| 8,524,286 B2 | 9/2013 | Smothers |
| 8,603,515 B2 | 12/2013 | Whittle |
| 2003/0017216 A1 | 1/2003 | Schmidt et al. |
| 2004/0049059 A1 | 3/2004 | Mueller |
| 2008/0103193 A1 | 5/2008 | Castor et al. |
| 2008/0119544 A1 | 5/2008 | Guy et al. |
| 2008/0139667 A1 | 6/2008 | Robson et al. |
| 2010/0092585 A1 | 4/2010 | Smothers |
| 2010/0249223 A1 | 9/2010 | Di Marzo et al. |
| 2011/0256245 A1 | 10/2011 | Rosenblatt et al. |
| 2012/0264818 A1 | 10/2012 | Newland |
| 2013/0079531 A1 | 3/2013 | Barringer |
| 2013/0251824 A1 | 9/2013 | Hospodor et al. |
| 2015/0105455 A1 | 4/2015 | Bjorncrantz |

FOREIGN PATENT DOCUMENTS

| | | |
|---|---|---|
| CN | 102186487 A | 9/2011 |
| CN | 102698045 A | 10/2012 |
| WO | WO 2010/045243 A1 | 4/2010 |
| WO | WO 2013/025916 A2 | 2/2013 |

OTHER PUBLICATIONS

Small et al., "Hemp: A New Crop with New Users for North America. Trends in new crops and new uses", 2002, J. Janick and A. Whipkey (eds.), ASHS Press, Alexandria, VA.
International Search Report and Written Opinion of PCT/US2015/019699 dated Jun. 8, 2015.

*Primary Examiner* — Michael V Meller
(74) *Attorney, Agent, or Firm* — Polsinelli PC

(57) ABSTRACT

The present invention provides methods of extracting Cannabis plant material through use of aloe, compositions comprising the resulting Cannabis aloe extracts, methods of using the extracts to ameliorate skin conditions, and applicators for applying the extracts topically.

14 Claims, No Drawings

CANNABIS EXTRACTION METHOD AND COMPOSITIONS

CROSS REFERENCE TO RELATED APPLICATIONS

This application is a Continuation of application Ser. No. 15/037,817 filed on Mar. 10, 2015, which is the National Phase filing under 35 U.S.C. § 371 of PCT/US2015/019699 filed on Mar. 10, 2015; and this application claims the benefit of U.S. Provisional Application No. 61/968,893 filed on Mar. 21, 2014. The entire contents of each application are hereby incorporated by reference.

FIELD OF THE INVENTION

The present invention pertains to methods of extracting materials from biological sources, and particularly from plant matter for cosmetic and medicinal applications.

BACKGROUND AND DESCRIPTION OF RELATED ART

Since the earliest days of mankind plants have been used as sources of pharmacologically active materials. One such plant is *Cannabis sativa*, colloquially known as marijuana, which contains such pharmacologically-active substances as $\Delta^9$-tetrahydrocannabinol and other cannabinoids, which historically were ingested by smoking dried leaves of *Cannabis sativa*.

For medical and cosmetic purposes use of crude plant material poses a number of problems. First, it renders the dosage unknown and potentially highly variable. Second, the pharmacologically-active material may well constitute only a small proportion of the plant in question. Third, the desired pharmacologically-active material may well be admixed with toxic or otherwise undesirable adulterants. For this reason, it is often desirable to extract the desired pharmacologically-active material from its biological source. Such considerations prompted, e.g., the extraction of salicylic acid from willow bark in the mid-eighteenth century, and to the extraction of taxol from the bark of the Pacific yew tree in the mid-twentieth century U.S. Pat. No. 6,730,519 to Elsohly and Ross discloses a method of extraction involving use of non-polar solvents and purification by column chromatography on alumina columns.

US20030017216, filed by Schmidt and Coco, discloses an extraction method that uses various organic solvents but with a curtailed extraction period to extract primarily the surface structures of the plant.

U.S. Pat. No. 7,622,140 to Whittle et al. discloses an extraction method that uses hot air to volatilize cannabinoids.

U.S. Pat. No. 7,344,736 to Whittle et al. discloses an extraction method that uses sub-critical $CO_2$ to extract cannabinoids from *Cannabis* plant material, while US20040049059, filed by Mueller and Mueller, discloses a supercritical $CO_2$ extraction method, as does. Similarly, US20080103193, filed by Castor et al., discloses use of super- or near-critical carbon dioxide, nitrous oxide, ethylene, ethane, propane and chlorodifluoromethane, with or without organic co-solvents, as extractants for Cannabis plant material.

US20110256245, filed by Rosenblatt et al., discloses an extraction method for *Cannabis* flower trimmings with trichomes (glandular hairlike appendages) involving covering the trimmings with cold water.

US20120264818, filed by Newland, discloses extraction of Cannabis plant material with dimethylsulfoxide, and the use of the resulting extract as a topically applied composition for the treatment of various skin ailments such as dermatitis.

U.S. Pat. No. 8,343,553, to Hospodor, discloses a device for preparing extracts of *Cannabis* plant material, as does US2013/0251824, filed by Hospodor and Rapp.

US2013/0079531, filed by Barringer, discloses a process for rapid extraction of *Cannabis* plant material through brief contact with an organic solvent below room temperature to minimize the extraction of non-cannabinoid contaminants.

U.S. Pat. No. 8,337,908, to Letzel et al., discloses use of *Cannabis* extracts for, inter alia, topical use in treatment of various skin ailments, such extracts being prepared by a variety of known extraction methods and extractants.

U.S. Pat. No. 8,603,515, to Whittle, discloses pharmaceutical formulations of cannabinoids for administration via a pump action spray.

U.S. Pat. No. 8,512,767 to Ross discloses *Cannabis*-derived compositions suitable for sublingual aerosol or spray delivery.

US2008/0119544, filed by Guy and Pertwee, discloses various therapeutic uses of cannabinoid extracts, as does US2008/0139667, filed by Robson and Guy. US2010/0249223, filed by Di Marzo et al., discloses the therapeutic and prophylactic use of cannabinoid extracts in connection with, inter alia, cancer of the skin.

U.S. Pat. No. 8,524,286, to Smothers, discloses use of aloe to extract cardiac glycosides from *Nerium oleander*.

Each of the references above is hereby incorporated by reference in its entirety.

While the possession or use of *Cannabis* has been illegal in the United States since 1937, the medicinal properties of cannabinoids (e.g., for treatment of glaucoma) have become increasingly appreciated, which has spurred efforts to facilitate the legal and controlled medical use of cannabinoids. Extraction of cannabinoids and tetrahydrocannabinol from *Cannabis* plant material facilitates their use clinically by allowing administration of compositions of known and/or predetermined potency and purity. Accordingly, a need exists for a way to effectively extract pharmacologically-active compounds from plants of the genus *Cannabis*, and in particular using an extractant which itself is cosmetically acceptable or beneficial.

SUMMARY OF THE INVENTION

The present invention provides a method to extract cannabinoids such as cannabadiols and $\Delta^9$-tetrahydrocannabinols from plant material derived from a plant of the genus *Cannabis* using aloe as extractant, such as that derived from Aloe vera, to yield a Cannabis aloe extract. The extract is useful for, inter alia, ameliorating skin conditions. In further embodiments, the invention provides pharmaceutical or cosmetic compositions comprising the resulting *Cannabis* aloe extract, methods of using such compositions, and applicators comprising the extracts or the compositions.

DETAILED DESCRIPTION OF THE PREFERRED EMBODIMENTS

Definitions

Unless otherwise specified, technical terms take the meanings specified in the McGraw-Hill Dictionary of Scientific and Technical Terms, 6th edition.

"Plant material" refers to any part of a plant, and includes bark, wood, leaves, stems, roots, flowers, fruits, seeds, berries as well as exudates, which optionally has been dried, cut into pieces, milled, or powdered.

"Cannabis" refers to plants of the genus *Cannabis*. The genus includes *Cannabis sativa*, (sometimes divided into the two subspecies *Cannabis indica* and *Cannabis ruderalis*), as well as all variants, chemovars, and subspecies thereof, and also plants resulting from genetic crosses, self-crosses or hybrids thereof.

"*Cannabis* plant material" refers to plant material derived from a plant of the genus *Cannabis*. It includes Cannabis leaves and stems, which preferably may be cut into pieces, milled, dried, and/or powdered to facilitate extraction.

"Aloe" refers to mucilage derived from a plant of the genus *Aloe*, which includes the species *Aloe arborescens, Aloe aristata, Aloe dichotoma, Aloe nyeriensis, Aloe varvegata, Aloe wildii*, and *Aloe barbadensis miller* among others, where "mucilage" here refers to the mucilageneous gel obtained from within the leaves of plants of the genus *Aloe*. Mucilage derived from an *Aloe* species, such as *Aloe barbadensis miller*, is obtained by methods well-known to those skilled in the art. For example, U.S. Pat. No. 4,957,907, which is hereby incorporated by reference in its entirety, describes in detail one procedure for producing aloe. Aloe so obtained can be used either in liquid form, or as a powder (prepared, e.g., by freeze drying) that upon addition to water reconstitutes the liquid form.

"Cannabinoids" as used here refers to pharmacologically-active compounds found in plants of the genus *Cannabis*, most prominently $\Delta^9$-tetrahydrocannabinol, $\Delta^8$-tetrahydrocannabinol, and cannabidiol, but also including cannabinol and cannabigerol.

"Lower alkyl" refers to $C_1$-$C_6$ linear, branched, and alicyclic hydrocarbons.

"Carrier" refers to a chemical compound, such as dimethylsulfoxide, that facilitates the incorporation of a compound into cells or tissues and/or provides a vehicle for application of the extract, e.g. to skin.

"Diluent" refers to aqueous solutions of salts and buffers introduced to a composition to modify the pH and/or osmotic strength of the composition, one example of which is phosphate buffered saline.

"Dermal agents" refers to substances added to compositions to facilitate their topical application. Examples include ingredients used in formulating cosmetics, such as an oily ointment, an aqueous ointment, a cream, a lotion (e.g., a cosmetic lotion, a face lotion), an emulsion, a pack, a soap, a face wash, a makeup (a body makeup, a face makeup), a spot cream, ointment or lotion, and combinations thereof.

"Skin condition" refers to various clinical pathologies and cosmetic maladies of the skin, and includes abscesses, dry skin, sun-damaged skin, aging skin, acne, actinic keratosis, age spots, liver spots, burns, sunburn, heat burn, radiation burn, cold sores, corns, eczema, psoriasis, ringworm, scabies, skin cancers, basal skin cancer, squamous skin cancer, melanoma skin cancer, skin tags, and/or warts.

"Pharmaceutically acceptable carriers" refer to substances that are biocompatible (i.e., not toxic to the host) and suitable for topical administration of a pharmacologically effective substance. Suitable pharmaceutically acceptable carriers include but are not limited to stabilizing agents, wetting and emulsifying agents, salts for varying osmolarity, encapsulating agents, buffers, and skin penetration enhancers. Examples of pharmaceutically acceptable carriers are described in Remington's Pharmaceutical Sciences (Alfonso R. Gennaro, ed., 18th edition, 1990).

The compositions may comprise one or more pharmaceutically acceptable carriers. Other ingredients well known in the art of preparing cosmetics and other products suitable for application for the skin can be used as pharmaceutically acceptable carrier. Examples include lipophilic compounds, such as glyceryl esters of a long-chain fatty acid (e.g., glyceryl monostearate, glyceryl monopalmitate, myristyl laurate, and myristyl palmitate), lanolin alcohol, palm oil, and other compounds known in the cosmetics art.

Extraction Method

In the process of the invention, Cannabis plant material is combined with an extractant which comprises, consists essentially of, or consists of aloe, to form a Cannabis aloe extract.

The extraction method comprises mixing *Cannabis* plant material with aloe in a ratio of about 1 to about 100 parts of aloe to one part of Cannabis plant material (w/w), and preferably 5-20 parts of aloe to one of *Cannabis* plant material (w/w), and most preferably about nine parts of aloe to one part of *Cannabis* plant material (w/w), although the most effective proportions for extraction can be determined by the skilled artisan for any particular plant material or extractant.

The extraction mixture can optionally be heated to a temperature of about 40° C. to about 100° C., for about one to 10 hours, but neither the exact temperature nor the time is critical to the extraction, but may enhance the degree of extraction. Similarly, the extraction mixture can be agitated during extraction by, e.g., stirring, shaking, vortexing, sonicating, or other method, the choice of which is not critical.

The extraction method can further optionally include use of additional extractants such as lower alkyl alcohols, ketones, and esters which form an extraction mixture along with aloe. Examples of suitable additional extractants include methanol, ethanol, propanol, n- and isopropanol, n-butanol, tert-butanol, acetone, methyl ethyl ketone, methoxyethanol, 2-butoxyethanol, diethyl ether, acetone, butanone, and ethyl acetate.

The aloe extract of Cannabis aloe extract so obtained may be, and preferably is, substantially separated from the remaining Cannabis plant material by, for example, filtration, separation, centrifugation, screening (for example through a 1 or 0.5 micron screen), and decantation or other separation methods including the use of filter screens, mesh, or fibrous materials or other man-made or materials found in nature the choice of which is not critical, of porous nature from various types of rock, sand, clay or charcoal type materials to facilitate the further separation of plant components, as known in the art. In addition, various lipids can optionally be removed from the *Cannabis* aloe extract by processes such as "winterization", viz., chilling (e.g., to −20° C.) followed by filtration to remove waxy ballast.

The Cannabis aloe extract is normally recovered as a liquid but may be converted and maintained for storage as a solid (e.g. freeze dried) which can be reconstituted to a liquid, for example by adding water.

For some purposes it may be desirable to produce *Cannabis* aloe extracts with differing proportions of the constituent cannabinoids. For example, in some contexts it may be desirable to have a higher proportion of cannabadiol than $\Delta^9$-tetrahydrocannabinol than in others. Such manipulation of the relative proportions of the various cannabinoids can be readily effected by changes in the extractant(s) or extraction conditions, and/or choice of particular *Cannabis* cultivars chosen for the relative proportions of cannabinoids they contain.

Pharmaceutical Compositions

*Cannabis* aloe extracts obtained as described above provide a basis for pharmaceutical compositions that comprise the *Cannabis* aloe extract and at least one pharmaceutically acceptable carrier. Another embodiment provides cosmetic compositions comprising a *Cannabis* aloe extract and at least one dermal agent.

The term "pharmaceutical composition" as used here refers to *Cannabis* aloe extract in combination with other chemical components, such as diluents, carriers, excipients and auxiliaries to facilitate topical application of the *Cannabis* aloe extract to an organism. The term "pharmaceutical composition" as used here includes cosmetic compositions and food or nutraceutical compositions, which are not necessarily intended for use in the treatment of a particular skin pathology. The inventive pharmaceutical compositions can be administered to the skin in the form of an ointment, a poultice, a plaster, a compress, a balm, an unguent, a salve, an emollient, and other forms suitable for administering substances to the skin.

Further, the inventive pharmaceutical composition can also be formulated for routes of administration other than topical. In some context, for example, it may be desirable to administer compositions based on *Cannabis* aloe extracts orally, sublingually, buccally, vaginally, or rectally, for which purpose suitable formulations can be prepared, with diluents, carriers, excipients and auxiliaries selected for the contemplated route of administration. As such, the present invention contemplates tablets, capsules, liquid gels, suppositories, and other well-known dosage forms as vehicles for administration of pharmaceutical compositions comprising *Cannabis* aloe extracts.

Techniques for formulating and administrating the pharmaceutical compositions may be found in "Remington's Pharmaceutical Sciences," Mack Publishing Co., Easton, Pa., 18th edition, 1990.

The pharmaceutical compositions described herein can be administered to a human patient per se, or as part of other pharmaceutical compositions where they are mixed with other active ingredients, as in combination therapy, or suitable carriers or excipient(s).

Methods of Treatment

This application also discloses a method of treating or otherwise ameliorating a skin condition (as defined above) comprising applying an efficacious amount of the inventive pharmaceutical composition to the skin of a subject. In this context, treating a skin condition does not necessarily imply medical treatment, and thus for example may include providing a benefit typically associated with the application of a cosmetic, such as soothing, softening or moisturizing the skin, facilitating the toning, and tightening of skin, reduction of pore size and reduction of appearance of blemishes, spots and wrinkles, and/or hair.

In practice an efficacious amount of the pharmaceutical composition means applying *Cannabis* aloe extract containing sufficient cannabinoids to prevent, alleviate or ameliorate symptoms of disease in the subject being treated. Determination of what constitutes an efficacious amount is within the capability of those skilled in the art, and may involve assaying a given portion of Cannabis aloe extract for its cannabinoid content.

Methods of assaying cannabinoids, especially through immunological methods, are well-known in the literature, and allow ready determination of the cannabinoid concentration in a Cannabis aloe extract sample. U.S. Pat. No. 5,747,352, to Yan et al., U.S. Pat. No. 5,910,419, to Johnson et al., U.S. Pat. No. 6,720,192 to Viel and Ensing, U.S. Pat. No. 7,749,712, to Pull et al., and U.S. Pat. No. 8,518,653, to Takkinen et al., each of which is hereby incorporated by reference in its entirety, each describe methods of determining the amount and relative proportion of cannabinoids in a given sample.

The amount of the inventive pharmaceutical composition administered will generally be dependent on the subject being treated, on the subject's weight, the nature and severity of the skin condition, the manner of administration, the concentration and identity of the cannabinoids in the *Cannabis* aloe extract, and the judgment of the prescribing physician.

Applicator

Further embodiments of the invention provide an applicator to be used in conjunction with the Cannabis aloe extracts or pharmaceutical compositions, wherein the applicator contains the extract or the pharmaceutical composition and is used to apply it to the skin of a subject. The applicator can take the form of a hand-actuated pump, an aerosol can, a patch, or a roll-on device such as those used for application of deodorants.

EXAMPLES

Example 1

Dried leaves and stems of *Cannabis sativa* (100 g) were milled to a fine powder, weighed into a glass container and mixed with aloe derived from *Aloe barbadensis* leaf juice (900 g) that had been processed to a liquid with a maximum anthraquinone (aloin and/or aloe emodin) content of 1 ppm, pH of 3.7-4.1, and containing 0.1% potassium sorbate.

The resulting extraction mixture was agitated until homogeneous, and the container with the extraction mixture was placed into a temperature controlled water bath at 80-85° C. for five hours with no agitation. The conditioned extraction mixture was then covered and allowed to cool.

After the extraction mixture cooled, a portion of the mixture was separated from the residual plant material by decantation. The extract was then separated from any remaining plant material by straining. The extract was then agitated until homogeneous.

The extract was then filtered through a medium of approximately 1 micron porosity, followed by a second filtration through a medium of 0.5-1.0 micron porosity, and the resulting extract (substantially free of plant material) was stored in a sealed glass container at ambient temperature.

Example 2

An extract (substantially free of residual plant material) prepared as described in Example 1 was combined with a dermal agent in a ratio of 4 parts by weight of extract to 1 part by weight of dermal agent, based on the total weight of the pharmaceutical composition. The dermal agent contained Glycerin, Methyl Sulfonyl Methane, *Oryzo Sativa* (Rice Bran) Oil, *Ricinus Communis* (Castor) Oil, glyceryl stearate, styrene/acrylates copolymer, PEG-100 stearate, cetyl alcohol, dimethicone, carbomer, caprylyl glycol, glycerin, glyceryl caprylate, phenylpropanol, methyl paraben, tocopherol (vitamin E), and fragrance.

Those of skill in the art will appreciate that numerous and various modifications can be made without departing from the spirit of the present invention. The various embodiments of the present invention described herein are illustrative only and not intended to limit the scope of the present invention.

The invention claimed is:

1. A method of preparing *Cannabis* Aloe extract consisting essentially of:
   a) providing *Cannabis*, which has been processed by one or more of the following steps of cut into pieces, milled, dried and powdered, with an extractant consisting essentially of Aloe leaf liquid wherein the extractant is in liquid form and/or if the Aloe is in powdered form the Aloe is reconstituted to liquid form with water,
   b) extracting the *Cannabis* by heating at temperatures from about 25° C. to about 100° C. for about 1 to about 10 hours, thereby forming a *Cannabis* Aloe extract;
   c) separating the *Cannabis* Aloe extract from lipids, waxy ballast and plant material by a method from the group of filtration, centrifugation, screening, decantation and combinations thereof, and
   d) processing the *Cannabis* Aloe extract by winterization to provide the *Cannabis* Aloe extract which consists essentially of cannabinoids.

2. The method of claim 1, further consisting essentially of separating the plant material from the *Cannabis* aloe extract to recover a *Cannabis* aloe extract substantially free of plant material.

3. The method of claim 1, wherein the *Cannabis* is derived from a species selected from the group consisting of *Cannabis sativa*, *Cannabis indica*, and *Cannabis ruderalis*.

4. The method of claim 1, wherein the *Cannabis* is derived from *Cannabis sativa*.

5. The method of claim 1, wherein about one part to about 50 parts by weight of *Cannabis* is mixed with about one part to about 100 parts by weight of aloe.

6. The method of claim 1, wherein the extraction mixture further consists essentially of a least one additional extractant selected from the group consisting of alcohols, ketones, and esters.

7. The method of claim 6, wherein the additional extractant is selected from the group consisting of methanol, ethanol, propanol, n- and iso-propanol, n-butanol, tert-butanol, acetone, methyl ethyl ketone, methoxyethanol, 2-butoxyethanol, diethyl ether, acetone, butanone, and ethyl acetate, and mixtures thereof.

8. The method of claim 1, wherein c) is selected from the group consisting of filtration, centrifugation, and decanting or combinations thereof.

9. The method of claim 1, which further consists essentially of converting the *Cannabis* aloe extract to a solid form.

10. The method of claim 1, wherein the *Cannabis* aloe extract is converted to a solid form by drying.

11. The method of claim 1, wherein the *Cannabis* aloe extract is converted to a solid form by freeze drying.

12. The method of claim 1, wherein the cannabinoids consists essentially of cannabadiol and $\Delta^9$-tetrahydrocannabinol.

13. The method of claim 1, wherein weight ratio of the Aloe leaf liquid to the *Cannabis* is about 1:1 to about 100:1.

14. The method of claim 1, wherein weight ratio of the Aloe leaf liquid to the *Cannabis* is about 5:1 to about 20:1.

* * * * *